United States Patent [19]
Yoon et al.

[11] Patent Number: 5,897,563
[45] Date of Patent: Apr. 27, 1999

[54] METHOD FOR USING A NEEDLE HOLDER TO ASSIST IN SUTURING

[75] Inventors: InBae Yoon, Phoenix, Md.; Ronald J. Brinkerhoff, New Richmond, Ohio; David Stefanchik, Mason, Ohio; Jeffrey S. Swayze, Cincinnati, Ohio; Bryan Knodel, Flag Staff, Ariz.; Rudolph H. Nobis, Mason, Ohio

[73] Assignee: Ethicon Endo-Surgery, Inc., Cincinnati, Ohio

[21] Appl. No.: 08/947,115

[22] Filed: Oct. 8, 1997

[51] Int. Cl.⁶ ..................................................... A61B 17/04
[52] U.S. Cl. ........................... 606/144; 606/147; 606/148
[58] Field of Search ................................... 606/147, 145, 606/144, 139, 148

[56] References Cited

U.S. PATENT DOCUMENTS

| | | | |
|---|---|---|---|
| 4,635,638 | 1/1987 | Weintraub et al. | 606/147 |
| 5,100,421 | 3/1992 | Christoudias | 606/147 |
| 5,152,769 | 10/1992 | Baber | 606/145 |
| 5,171,257 | 12/1992 | Ferzli | 606/205 |
| 5,224,948 | 7/1993 | Abe et al. | 606/147 |
| 5,261,917 | 11/1993 | Hasson et al. | 606/139 |
| 5,300,082 | 4/1994 | Sharpe et al. | 606/147 |
| 5,389,103 | 2/1995 | Melzer et al. | 606/144 |
| 5,397,325 | 3/1995 | Della Badia et al. | 606/144 |
| 5,454,823 | 10/1995 | Richardson et al. | 606/148 |
| 5,480,406 | 1/1996 | Nolan et al. | 606/147 |
| 5,759,188 | 6/1998 | Yoon | 606/147 |

FOREIGN PATENT DOCUMENTS

| | | |
|---|---|---|
| 0482881A1 | 4/1992 | European Pat. Off. . |
| 0337579 | 4/1904 | France .................................... 606/144 |
| 0395073 | 8/1973 | U.S.S.R. ............................... 606/147 |
| 2260704 | 9/1991 | United Kingdom . |

*Primary Examiner*—Michael Buiz
*Assistant Examiner*—Lien Ngo
*Attorney, Agent, or Firm*—Dean Garner

[57] ABSTRACT

In accordance with the present invention there is provided a method for suturing tissue using a needle holder device, The device includes a handle for holding it, the handle has distal and proximal ends. The device also has right and left arms extending distally from the handle. The arms of the device have proximal ends attached to the handle and distal ends having grippers attached thereto for gripping and releasing a needle. The device includes at least one mechanism for moving the distal ends of the arms closely adjacent to one another and for passing the needle from one gripper to the other and thereafter for moving the distal ends of the arms further apart from one another. The right gripper is holding a needle having a suture attached thereto. The method first involves moving the distal ends of the arms apart from one another and manually inserting the needle into the tissue and back out again. Thereafter, the method involves actuating the mechanism so as to move the arms closely adjacent one another so that the left gripper holds the needle, the right gripper releases the needle. Then the method involves moving the distal ends of the arms further apart from one another. Lastly, the method involves removing the needle from the tissue.

4 Claims, 17 Drawing Sheets

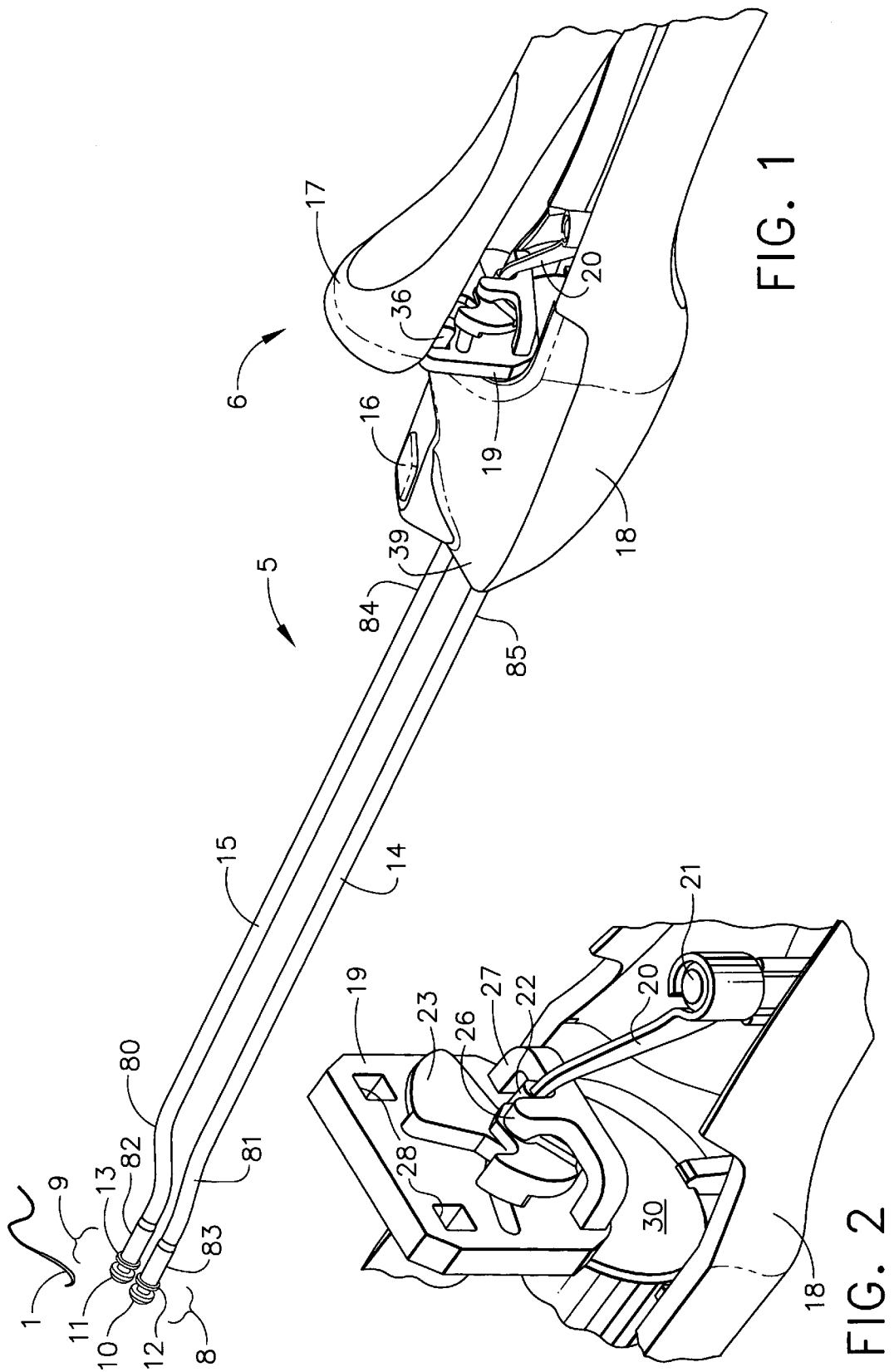

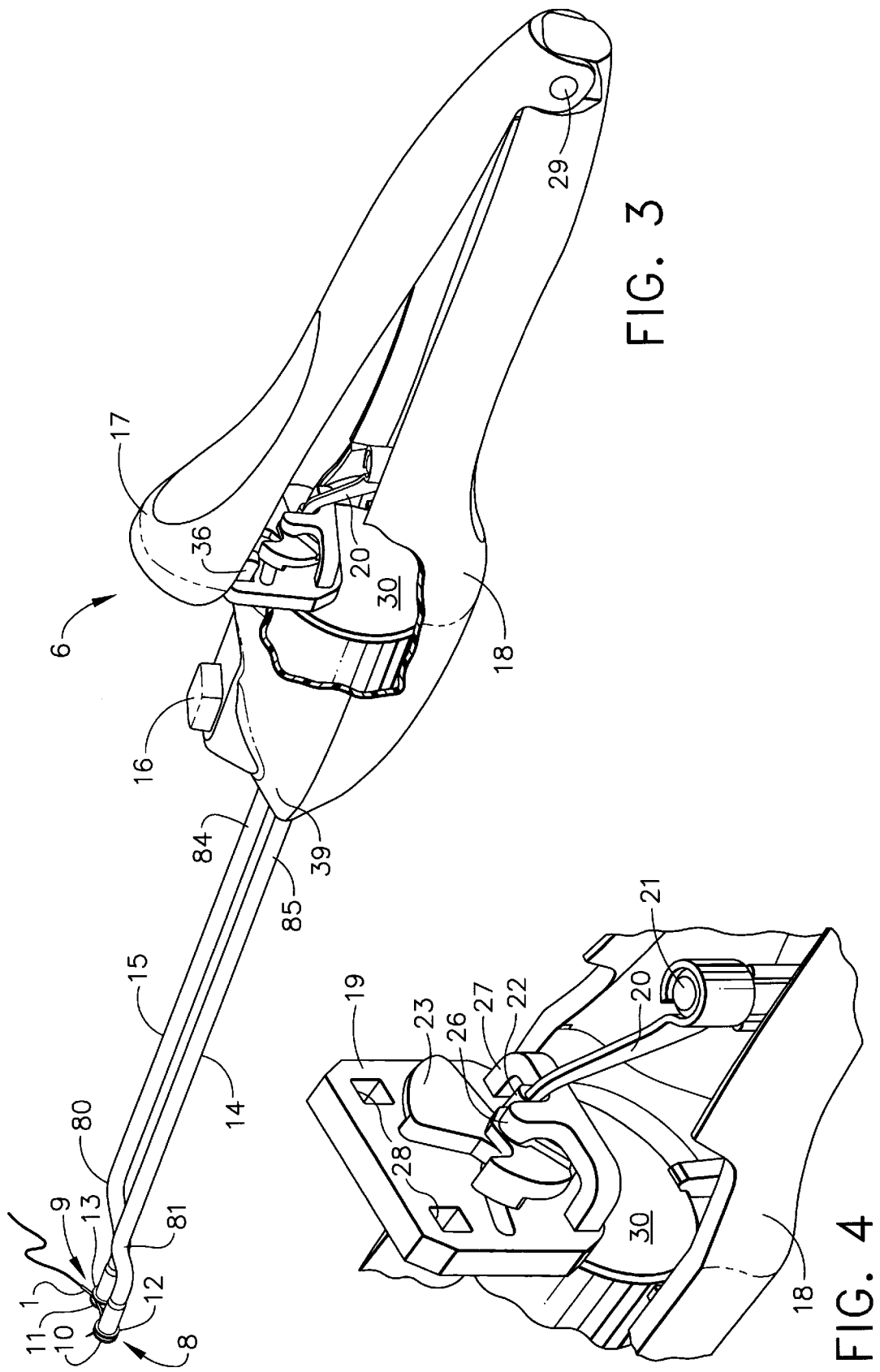

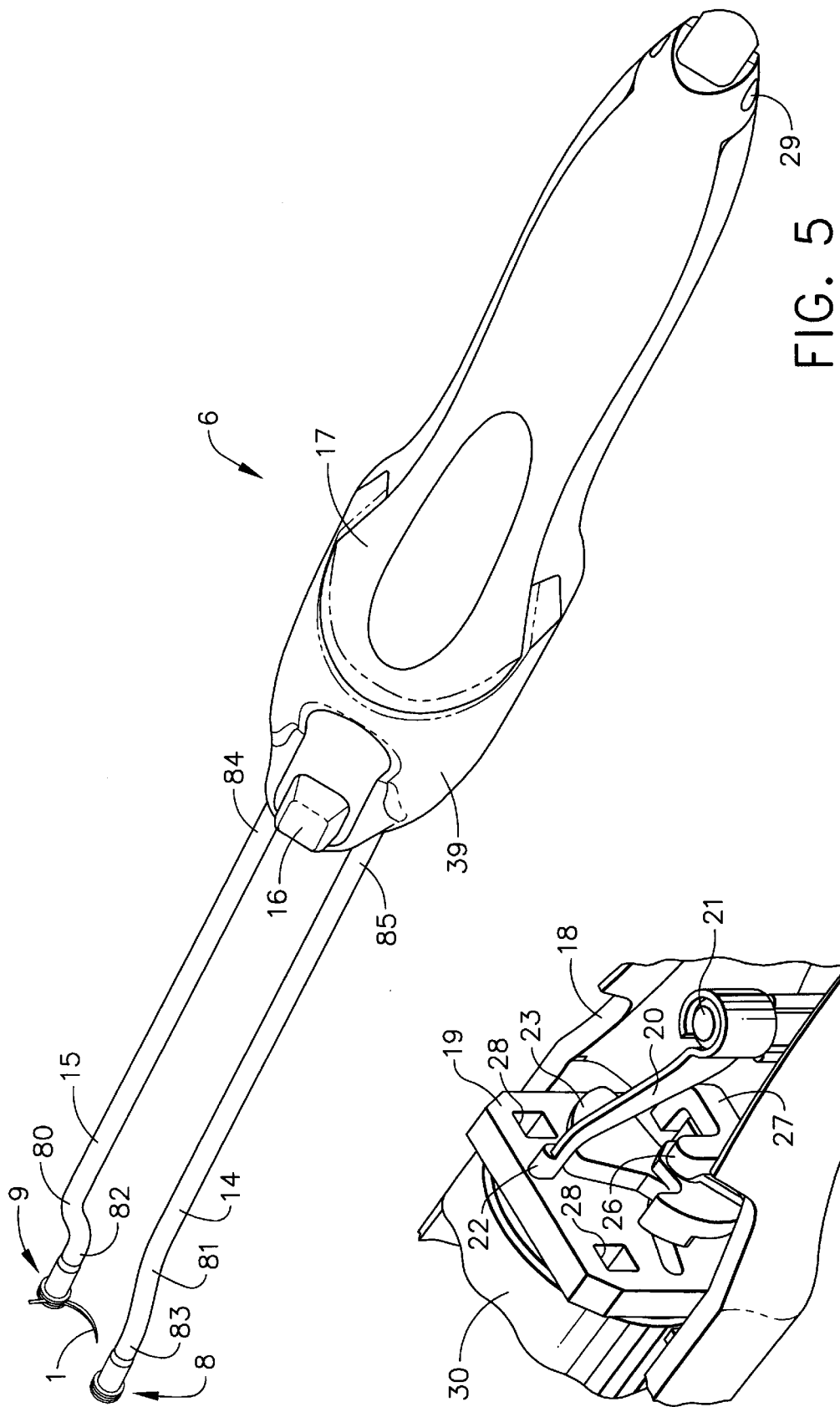

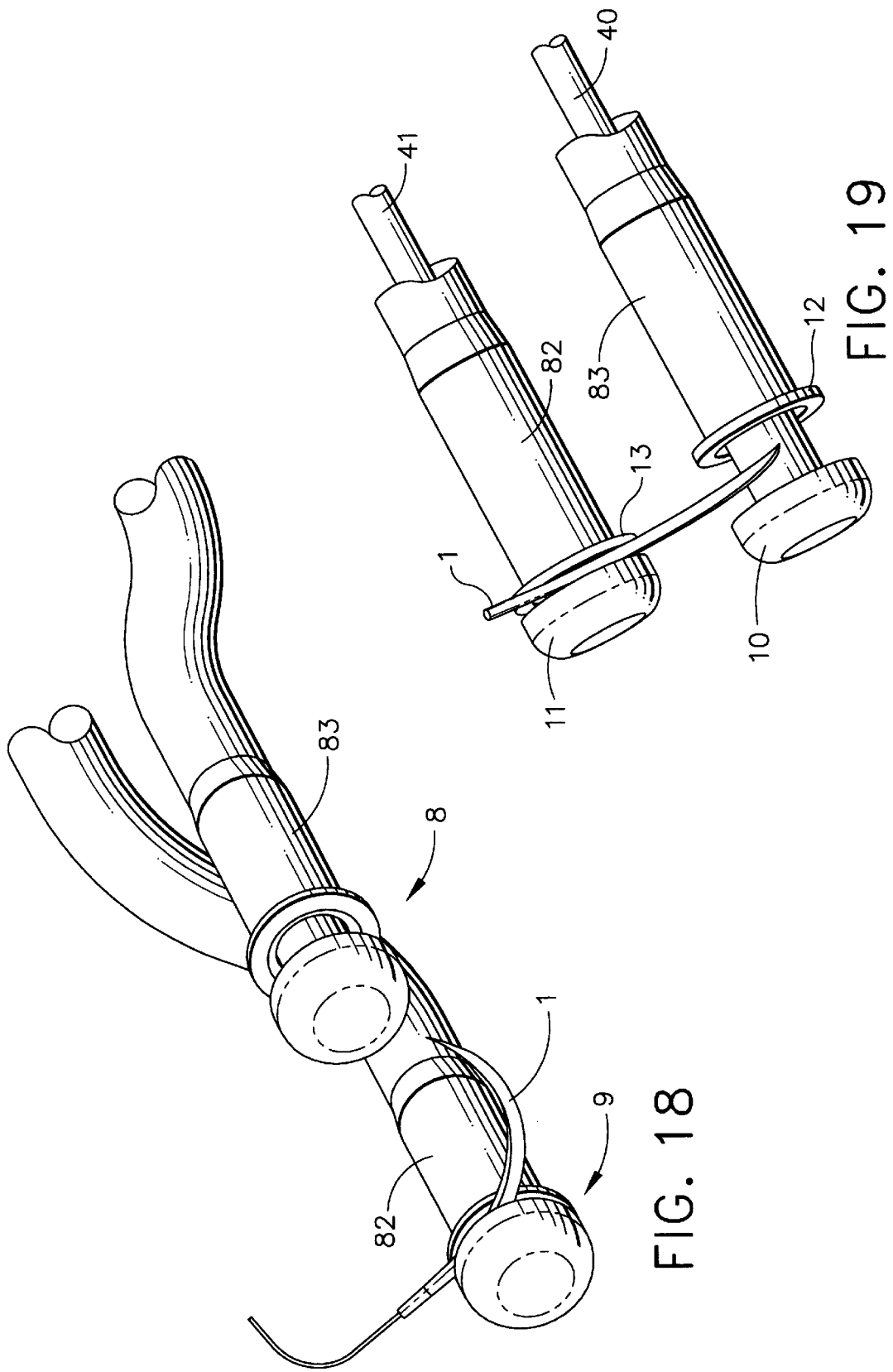

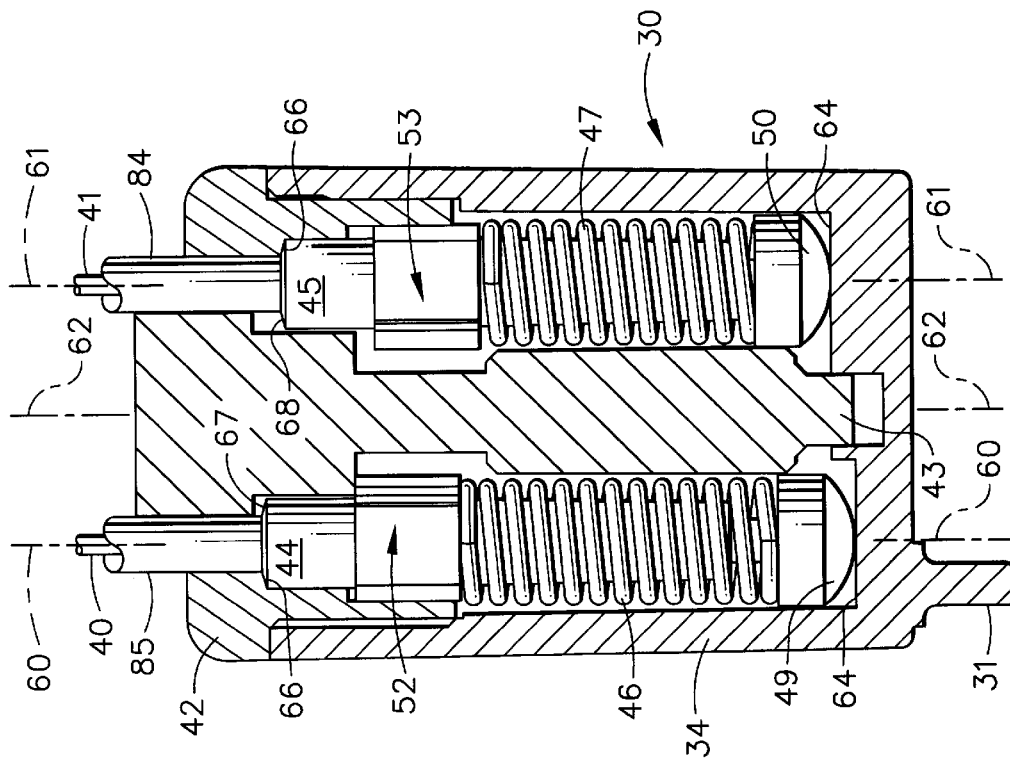
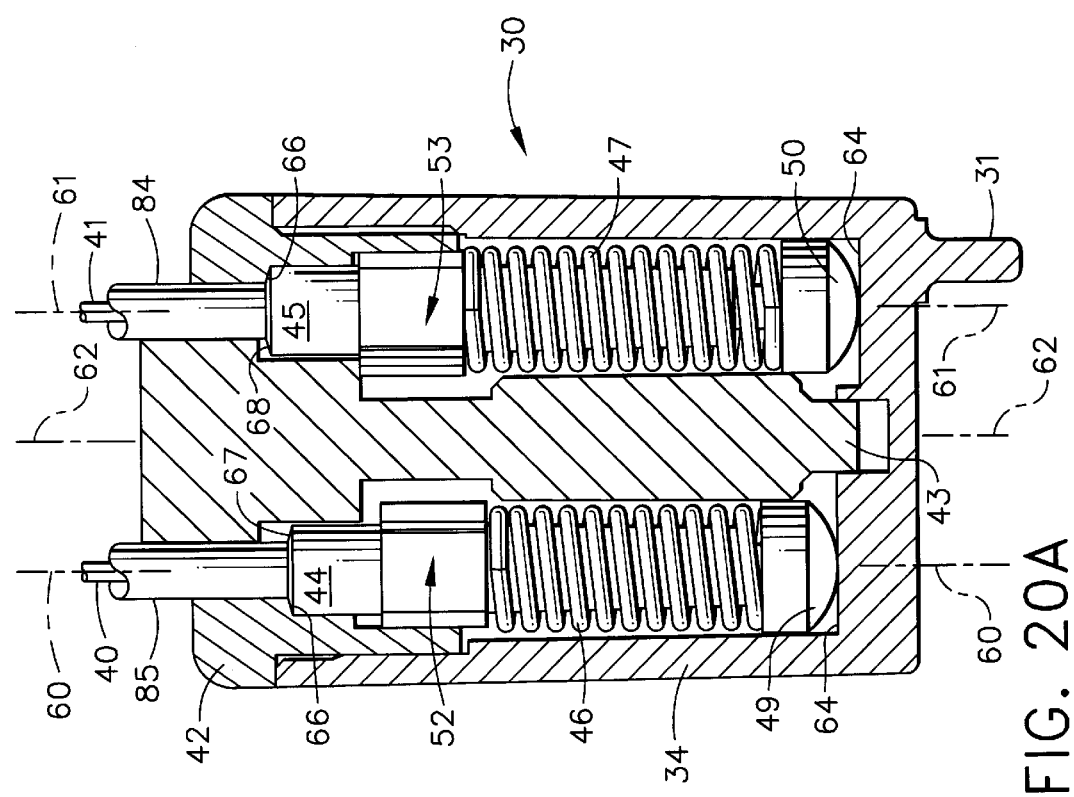

METHOD FOR USING A NEEDLE HOLDER TO ASSIST IN SUTURING

FIELD OF THE INVENTION

The present invention relates to the field of medicine and more particularly to surgery. More specifically, the present invention relates to surgical devices and methods for suturing bodily tissues both for open surgical procedures and for endoscopic surgical procedures. The present invention especially relates to surgical devices and methods for joining hollow organs, e.g. the anastomosis of the small or large intestines, and blood vessels, for joining them together in end-to-end, end-to-side, or side-to-side fashion.

BACKGROUND OF THE INVENTION

It is common surgical practice to use bypass grafts to help reestablish coronary artery circulation when a portion of the coronary artery is stenosed. Such a procedure is typically referred to as a Coronary Artery Bypass Graft (CABG) procedure. Typically the graft vessel used in bypassing the stenosed portion of the coronary artery comprises one or more segments of the patient's saphenous vein which is taken from his leg. The saphenous vein is dissected free from the leg, its side branches tied off or ligated, and the vein removed. The vein graft is then washed free of blood, and cut into portions of suitable length. Each portion is then passed to the surgeon who trims the ends of the graft before anastomosing the graft to the aorta and the coronary artery. Other graft vessels such as the radial artery in the arm can also be used. In addition, it is common practice today for the surgeon to redirect one of the internal mammary arteries (IMA) in the chest to the stenosed portion of the left anterior descending (LAD) artery on the heart. The end of the IMA near the patient's diaphragm is transected, the artery is mobilized by dissection and ligation of side branches, and then the end is joined to the LAD, just distal to the blockage. For multiple bypass surgery, a combination of the redirection of the IMA and the grafting of vessels to the diseased coronary arteries is often used.

Some surgeons choose to complete all the proximal anastomoses to the aorta before commencing the distal anastomoses to the coronary arteries. In contrast, others choose to complete the distal anastomoses first. Regardless of the order, when undertaking the distal anastomoses to the coronary artery, it is important that the vessel graft be held steady and adjacent the coronary artery, with a minimum of vascular trauma and a minimum of visual and surgical obstruction by instruments in the narrow operative field.

The speed of performing such anastomoses can become extremely critical as well. Often the coronary artery is occluded during the procedure so that the anastomoses can be performed more easily. It is very important to reconnect the supply of blood to artery as soon as possible in order to minimize or prevent damage to the patient. Blood vessels are now normally anastomosed end-to-end or end-to-side by suturing techniques. Conventionally, to suture two vessels together, a surgeon passes the pointed tip of a curved suturing needle, having a suture attached to the blunt end, through the coronary artery wall from inside the lumen. The needle is then passed through the graft vessel wall from the outside. Then, the surgeon grasps the tip of the needle which has been forced through the tissues with fingers or a needle holder and pulls the needle through the tissues, the suture following the curved path of the needle. Usually a knot or button is present at the trailing end of the suture to anchor the first stitch. After the surgeon has pulled the suture entirely through the tissues to tension the first stitch, he or she then forces the tip of the needle through the coronary artery again, at a location spaced from the first stitch, until the needle again goes through the coronary artery and back out through the graft vessel. Again, he grasps the tip of the needle which has been forced through the tissues, applies tension to the needle pulls the entire suture through the tissues to complete the second stitch. This process is repeated again and again, with the surgeon tensioning the suture after each stitch to draw the tissues together thereby creating a running or continuous stitch, composed of individual thread loops, which extends around the graft vessel.

Needless to say, such suturing techniques are a tedious and time consuming ask. Suture anastomoses procedures generally take the skilled surgeon anywhere from ten to twenty minutes to complete for each anastomoses. An example of a device which was designed to help a physician in performing suturing can be found in U.S. Pat. No. 5,437,681 issued to Meade et al. on Aug. 1, 1995 and U.S. Pat. No. 5,540,705 issued to Meade et al. on Jul. 30, 1996, both of which are hereby incorporated herein by reference. However, there are a number of disadvantages to the device disclosed in those references. In those devices it is the device itself which drives the needle through the tissue. Many physicians do not like this design because they like to have more control of needle placement and feel the resistance of the needle passing through the tissue when doing the procedure. Surgeons want the speed and efficacy offered by the new devices, but also want to maintain the benefits of the traditional suturing techniques.

Presently, there are no known simple, yet foolproof, techniques for helping the physician perform the anastomoses more quickly and with greater precision than when using conventional instruments. The present invention provides a method which overcomes the shortcomings of the prior art and helps the physician to suture bodily tissues easily and quickly. It is especially useful for performing an easy and quick vascular anastomoses such as for a CABG procedure.

SUMMARY OF THE INVENTION

In accordance with the present invention there is provided a method for suturing tissue using a needle holder device, The device includes a handle for holding it, the handle has distal and proximal ends. The device also has right and left arms extending distally from the handle. The arms of the device have proximal ends attached to the handle and distal ends having grippers attached thereto for gripping and releasing a needle. The device includes at least one mechanism for moving the distal ends of the arms closely adjacent to one another and for passing the needle from one gripper to the other and thereafter for moving the distal ends of the arms further apart from one another. The right gripper is holding a needle having a suture attached thereto. The method first involves moving the distal ends of the arms apart from one another and manually inserting the needle into the tissue and back out again. Thereafter, the method involves actuating the mechanism so as to move the arms closely adjacent one another so that the left gripper holds the needle, the right gripper releases the needle. Then the method involves moving the distal ends of the arms further apart from one another. Lastly, the method involves removing the needle from the tissue.

BRIEF DESCRIPTION OF THE DRAWINGS

The foregoing and other aspects of the present invention will best be appreciated with reference to the detailed description of the invention in conjunction with the accompanying drawings, wherein:

FIGS. 1–10 depict the sequence of operation of the present invention;

FIG. 1 is a perspective view of the present invention showing a curved, surgical needle being placed into the distal end of the device while the loading button is being depressed;

FIG. 2 is an enlarged, partial view of the device depicted in FIG. 1, with the trigger and handle top removed for clarity;

FIG. 3 is a perspective view of the present invention and shows the curved, surgical needle held in the distal end of the device after the loading button has been released, and a portion of the handle top and bottom has been cut away to view the barrel;

FIG. 4 is an enlarged, partial view of the device depicted in FIG. 3, but with the trigger and handle top removed for clarity;

FIG. 5 is a perspective view of the present invention, showing the curved, surgical needle held in the distal end of the right arm and the distal end of the left arm swung laterally apart from the right arm after the trigger has been actuated to the down position;

FIG. 6 is an enlarged, partial view of the device depicted in FIG. 5, but with the trigger and handle top removed for clarity;

FIG. 7 is a perspective view of the present invention showing the curved, surgical needle held in the distal end of both the right and left arms after the trigger has been released to the up position;

FIG. 8 is an enlarged, partial view of the device depicted in FIG. 7, but with the trigger and handle top removed for clarity;

FIG. 9 is a perspective view of the present invention showing the curved surgical needle held in the distal end of the left arm while the distal end of the right arm has been swung laterally apart from the left after the trigger has been actuated to the down position;

FIG. 10 is an enlarged, partial view of the device depicted in FIG. 9, but with the trigger and handle top removed for clarity;

FIG. 18 is a perspective view of a curved, surgical needle in the distal end of the present invention as depicted in FIG. 5;

FIG. 19 is a perspective view of a curved, surgical needle in the distal end of the present invention in the configuration corresponding to FIG. 20A;

FIGS. 20A and 20B are top, cross-sectional views of the barrel as depicted in FIGS. 14A and 14B;

Figures 7, 8:
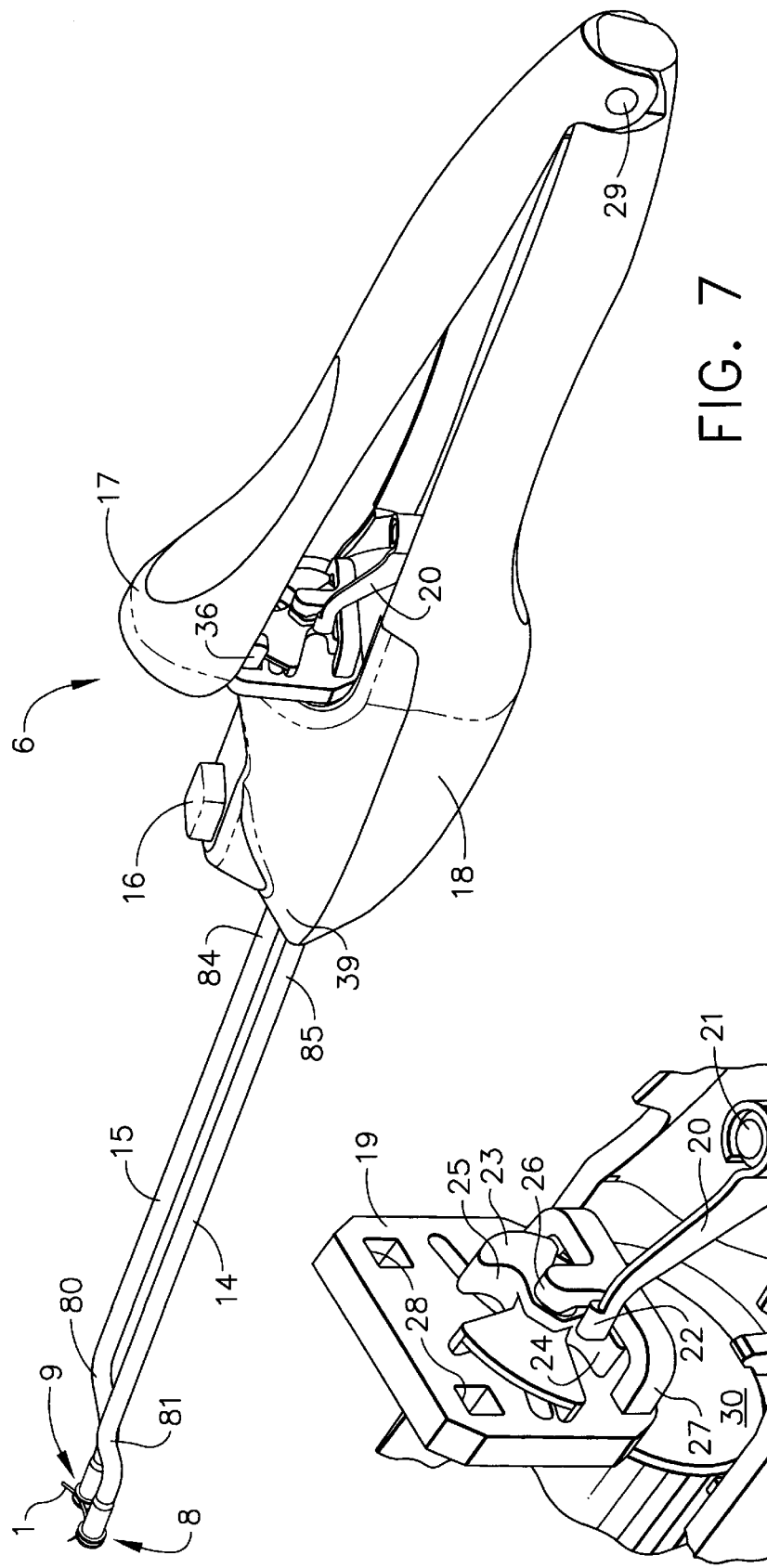

The drawings are not necessarily to scale.

DETAILED DESCRIPTION OF THE INVENTION

The suturing device of the present invention can be used to suture any type of anatomical tissue which may also be sutured using the traditional surgical methods described earlier. The device described herein is for use through any sufficiently-sized incision into the body, such as a mini-thoracotomy, but may also be used on external portions of the body such as for plastic surgery. It should also be clear to one of ordinary skill in the art that the present invention can be configured and provided with sealing means so as to make it possible to use through an endoscopic port. The device described herein is shown being used with a surgical needle having a particular radius of curvature. It may also be used with needles having other curvature radii or of many other shapes and sizes, including ski-shaped and straight needles, depending on the surgeon's preference for the surgical procedure being performed.

Referring now to the figures wherein like numerals indicate the same elements throughout the views there is shown in FIG. 1 a suturing device 5 in accordance with the present invention. Device 5 includes a handle 6 at its proximal end. Handle 6 includes a button 16 and a trigger 17 whose functions will be explained in detail below. Handle 6 is essentially a cylindrical body which is shaped ergonomically so that a surgeon may comfortably grip it and actuate the button 16 and trigger 17 with the same hand. The handle top 39, the handle bottom 18, the trigger 17, and the button 16 can be made of any substantially rigid, medical grade material but is preferably formed of a plastic such as polycarbonate. As will become apparent, this one hand manipulation of the device is advantageous in that it frees the surgeon's other hand for holding the tissue or other instrumentation. The length of the trigger 17 and the general shape of the handle 6 may vary from what is depicted in FIG. 1 in order to accommodate particular ergonomic requirements.

Extending distally from the handle 6 is a left tubular arm 14 and a right tubular arm 15. While the arms 14 and 15 are preferably round tubular, substantial longitudinal portions of them may have other cross-sectional shapes such as rectangular tubular or a C-shaped channel. The distal portions of arms 14 and 15 each have an offset bend section 80, 81 or dogleg so that the longitudinal axis of the distal arm ends 82, 83 are parallel to and offset from the longitudinal axis of the proximal arm ends 84, 85. The distal arm ends 82, 83 may differ from what is shown in that one or both of them may also be slightly angled with respect to the longitudinal axis of the device rather than be parallel to it. For example, both distal arm ends could be equally angled in towards each other. On the distal tip of left arm 14 is left gripper 8 comprising a left gripper head 10 and the left arm flange 12. Similarly, the distal tip of right arm 15 has a right gripper 9 comprising a right gripper head 11 and the right arm flange 13. As will be explained in greater detail below, grippers 8 and 9 are designed to alternately grip and release needle 1, as it is being passed from right arm 15 to left arm 14 and back again. The gripper heads 10, 11 and the arms 14, 15 may be made of a rigid, medical grade material including metal and plastic, but the preferred material is stainless steel.

Figure 23:
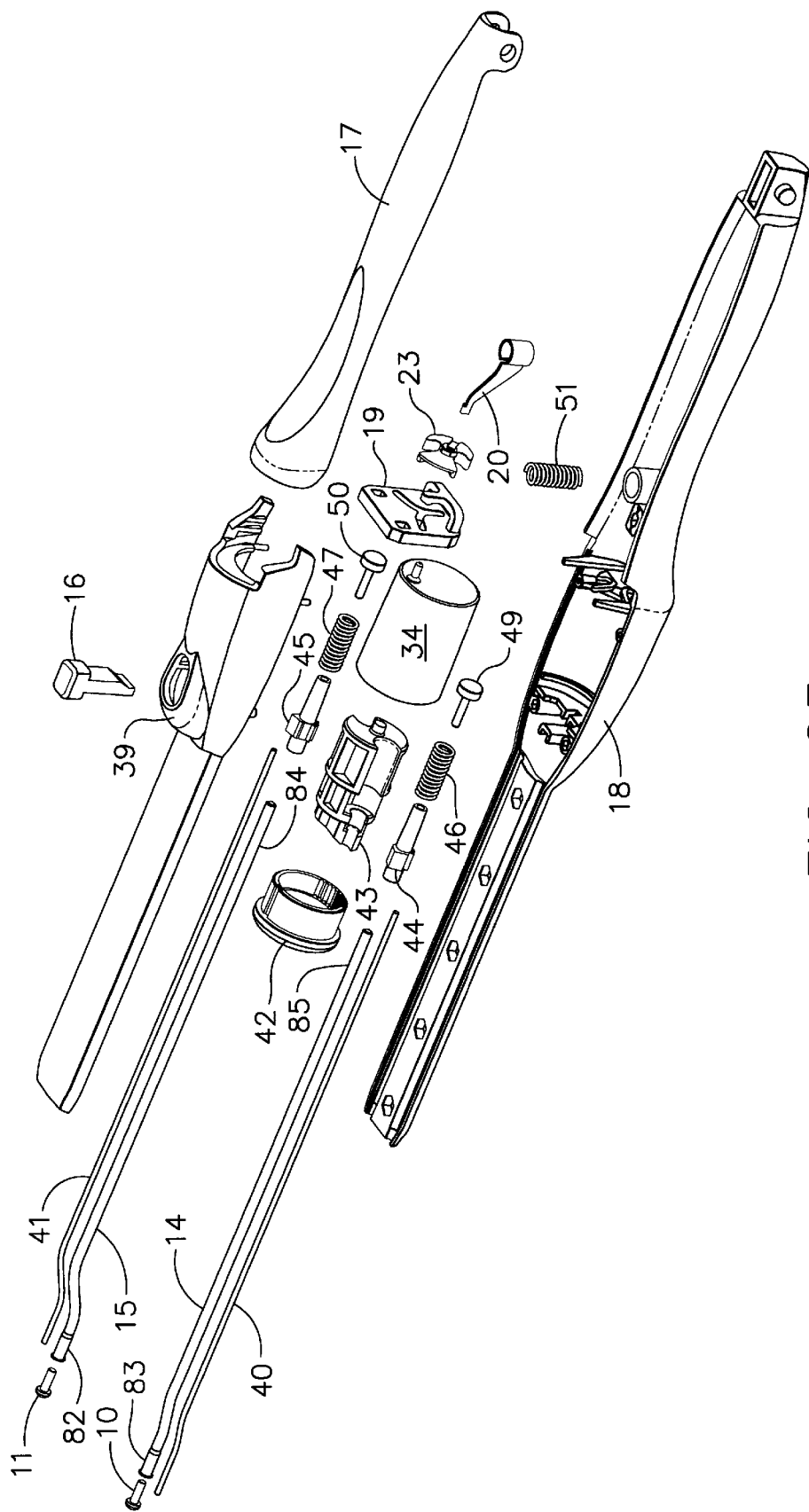
FIG. 23 is an exploded, perspective view of all the components of the present invention.
Figure 24:
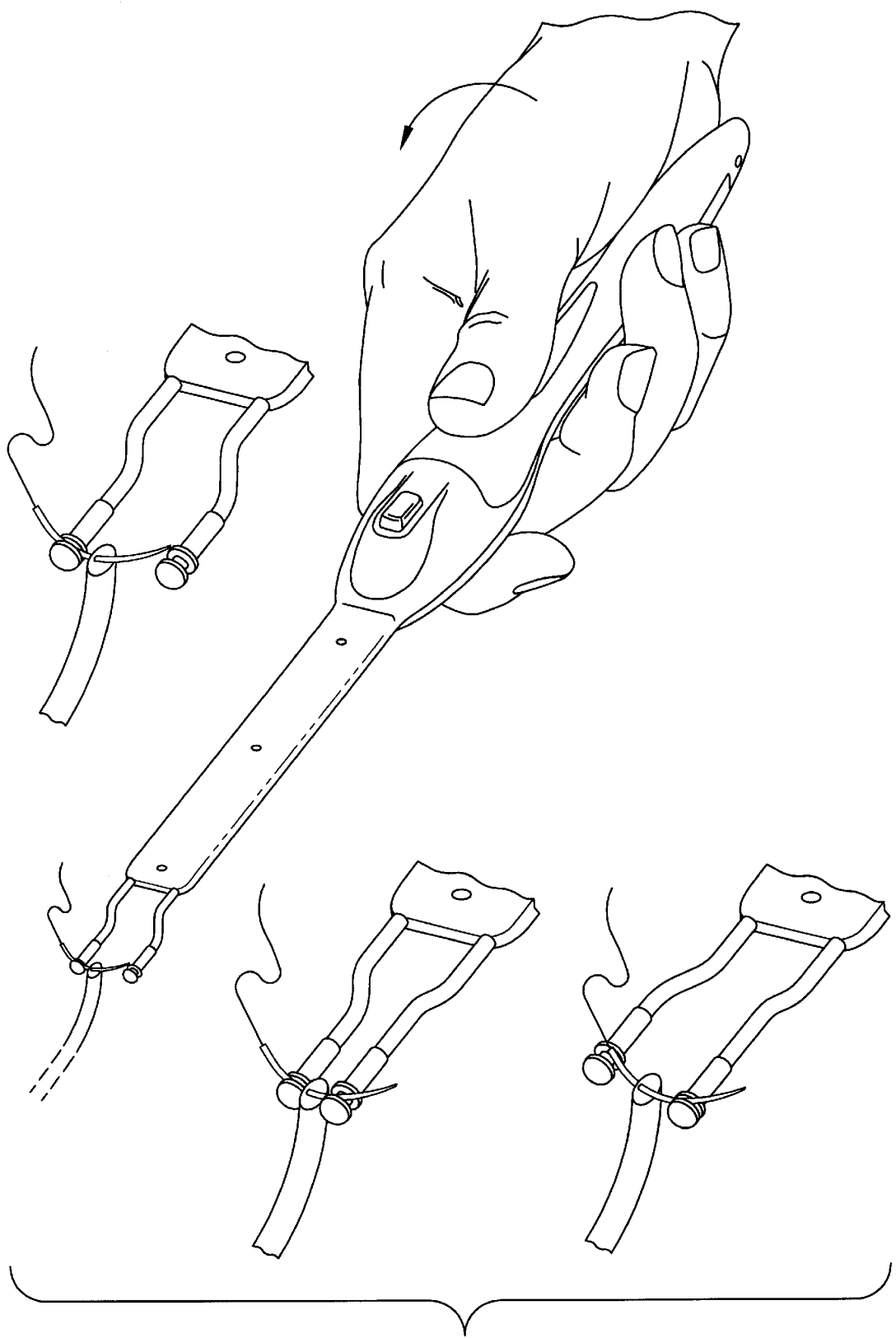
FIG. 24 shows perspective views of the present invention as it may be held by a surgeon and depicting a method for its use.

The proximal portion of the arms 14, 15 may be exposed as shown in FIGS. 1, 3, 5, 7 and 9, or may also be covered partially by the handle top 39 and handle bottom 18 as depicted in FIGS. 23 and 24. The length of the arms 14, 15 may vary considerably without resulting in a change of the function or usage of the device. Both of these variations are limited mostly by the overall rigidity of the device and the ease of manipulating it.

Figure 11B:
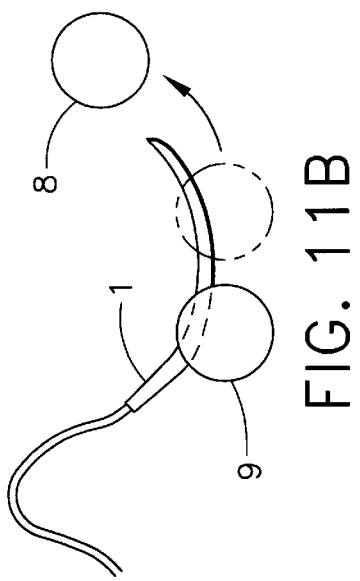
FIGS. 11A, 11B, 11C, 11D, and 11E are distal end views of the present invention depicting the sequence shown in FIGS. 3, 5, 7, 9, and 3 again, respectively.
Figure 11E:
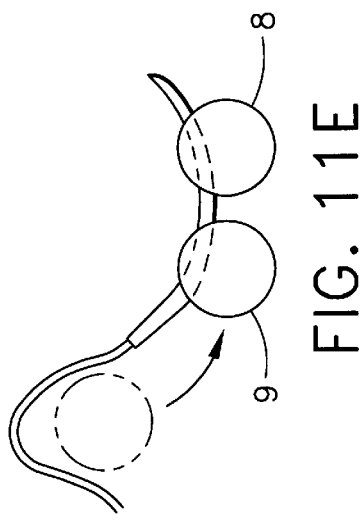
Figure 11C:
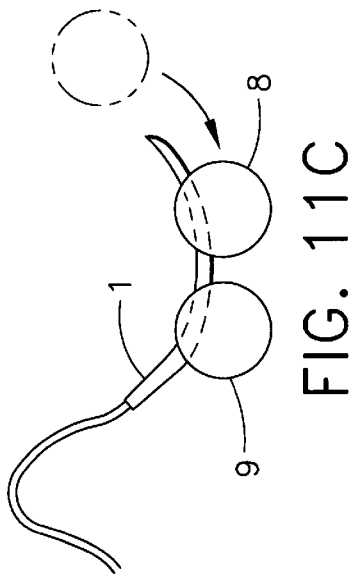
Figure 11A:
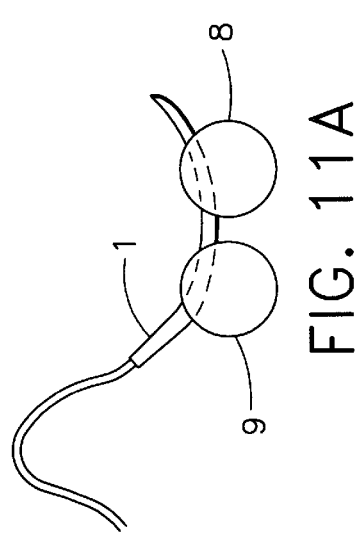
Figure 11D:
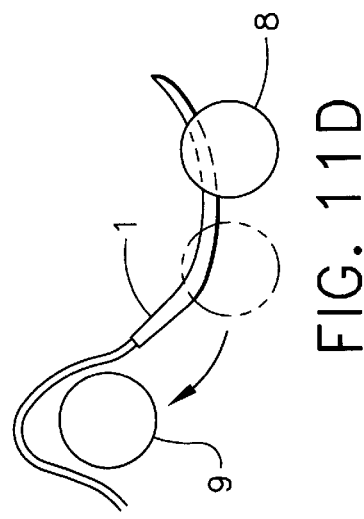
Figure 12A:
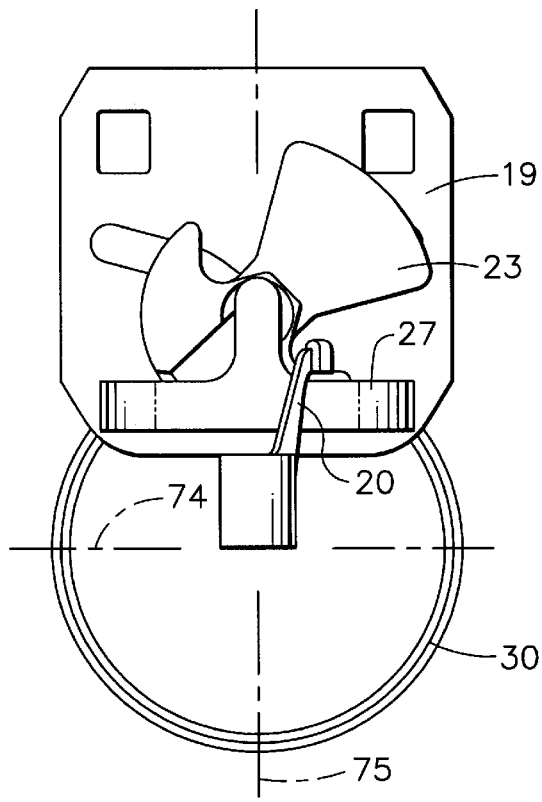
FIGS. 12A, 12B, 12C, and 12D are alternate views of FIGS. 2 and 4, 6, 8, and 10, respectively.
Figure 12C:
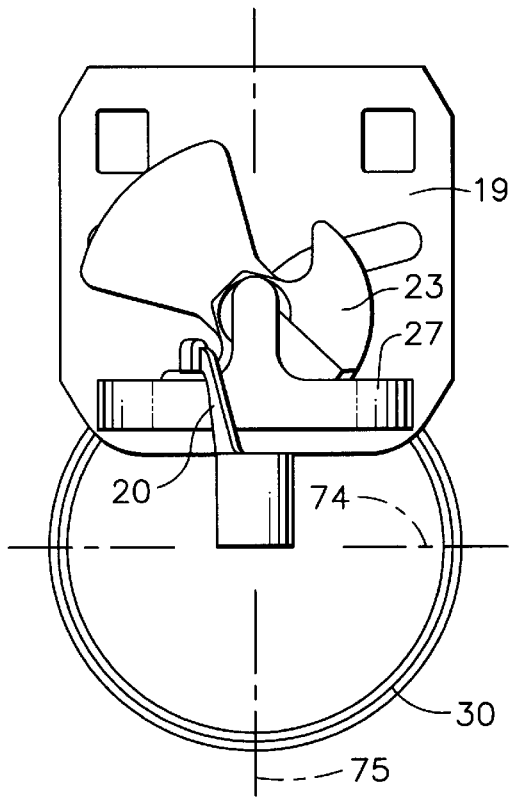
Figure 12B:
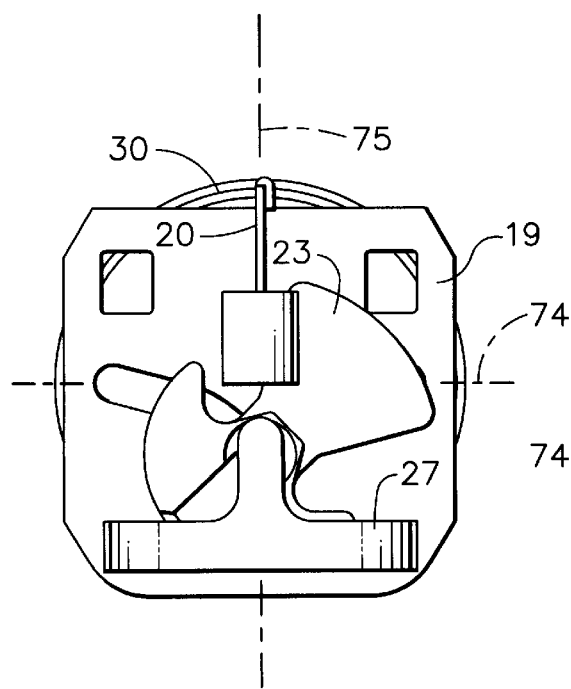
Figure 12D:
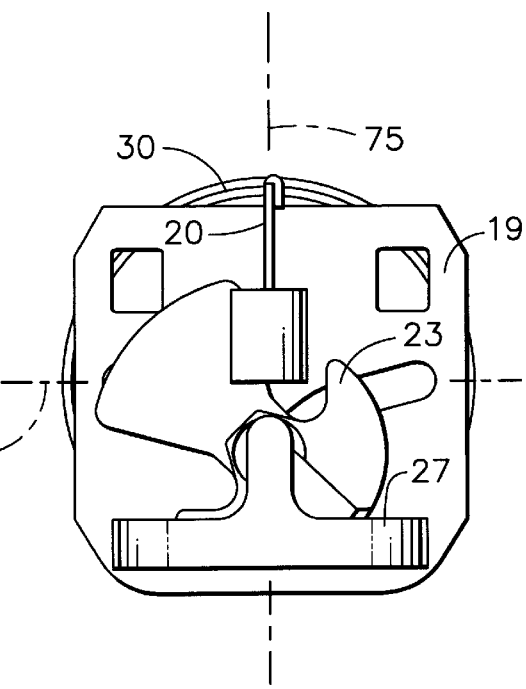

A brief and simplified description of how the device 5 works can best be accomplished by referring to FIGS. 11A–11E in conjunction with FIG. 1. In FIG. 11A the needle has just been loaded into the device so that both grippers 8 and 9 are holding the needle and the trigger 17 is in its up position (the trigger is explained in greater detail below). Thereafter, trigger 17 is pressed down and left gripper 8 releases the needle and swings away from the distal end of arm 15 as shown in FIG. 11B. The arc length of this swing motion is the same for each full actuation. However, it is possible to vary the design of the mechanisms later described so that this arc length can be significantly more or less than what is shown in FIG. 11B. The needle 1 can now be inserted into tissue and brought back out again by the surgeon's own action of twisting his wrists or the like. (This method of suturing using the present invention is depicted in FIG. 24.) Now right gripper 9 is on the side of the needle insertion site and left gripper 8 is on the side of the needle exit site. Therefore, the trigger is now released to its up position again so that left gripper 8 can grip the needle again as shown in FIG. 11C. As the trigger is pressed down this time, it is the right gripper 9 which releases the needle and is swung away from the left gripper 8 as shown in FIG. 11D. The arc length of this motion may be designed also to vary significantly as described for the other gripper. In this position the surgeon can now move the needle away from the tissue, pulling the suture therethrough so as to complete a stitch. Once this is done the trigger is again released so that gripper 9 grips the needle again and the process can be repeated. As will become apparent, the proximal arm ends 84, 85 never translate laterally with respect to each other. The swinging back and forth action of the left and right grippers is accomplished by axially rotating the arms 14, 15, causing the offset bend sections 80, 81 to move with respect to the handle 6.

The detail of how the above sequence of operation is accomplished by device 5 can best be described by referring to FIGS. 1, 3, 5, 7, and 9. Each of these figures has a corresponding illustration, FIGS. 2, 4, 6, 8, and 10 respectively, showing an enlarged portion of the mechanism in the handle 6 which controls the opening and closing of the grippers 8, 9 and the rotation of the arms 14, 15. Hereinafter, the needle will be described as being passed from the right gripper 9 to the left gripper 8 and them back to the right gripper 9, but it is also possible for the needle point to be directed in the opposite lateral direction, in which case the needle would be passed from the left gripper 8 to the right gripper 9 and then back to the left gripper 8. It should be noted also that the traditional surgical technique for pitching and catching a needle has been maintained in the present invention, in that a twisting motion of the surgeon's hand to penetrate the tissue with the needle as well as to pull the needle and trailing suture out of the tissue is still required. This is advantageous in that the surgeon still controls the precise placement and manipulation of the needle, yet is able to do so with one device rather than with two as when using traditional suturing techniques.

Referring to FIG. 1, a surgical needle with trailing suture is shown in the position it would be held as it is lowered into the left and right grippers 8 and 9. During this step, the button 16 is depressed by the surgeon, causing both the left and right gripper heads 10, 11 to be displaced distally from the corresponding left and right arm flanges 12, 13, creating a sufficient gap to allow loading of the needle. The actual mechanism for moving the left and right gripper heads will be explained in detail below. As will become apparent to those of ordinary skill in art as they read this description, the button 16 can also be pushed in order to load the needle 1 when the trigger is in the position shown in FIG. 7.

In FIGS. 1 and 2, the trigger 17 is not yet actuated and is in what is hereinafter referred to as its "up" position. FIG. 2 shows an enlarged view of some of the components of the handle and trigger mechanisms, with trigger 17 and handle bottom 39 removed for clarity. Two trigger prongs 36 (partially visible in FIG. 1, 3, and 7) project distally from the bottom side of trigger 17. These prongs fit slidably into toggle plate recesses 28 of toggle plate 19. When the trigger is actuated in the downward direction, pivoting about trigger pivot 29, the toggle plate and the trigger distal end move vertically together. The trigger is biased in the "up" position by trigger spring 51 (see FIG. 23.) In FIGS. 1, 2, since the trigger is in the "up" position for this step, the toggle plate 19 is also in the "up" position with respect to handle 6. Handle 6 further includes a toggle 23 which is pivotably attached to the toggle plate 19 and partially resides within a toggle plate rail 27. Toggle 23 has a left toggle surface 24 and a right toggle surface 25 (see FIGS. 8, 10.) In FIG. 4, toggle 23 is shown in its full, clockwise position.

Handle 6 further includes a toggle switch 20 mounted to handle bottom 18 by toggle switch mount 21. Toggle switch 20 has a tip 22, which is shown in FIG. 2 as bearing against right toggle surface 24 and toggle plate rail 27. Toggle switch 20 is attached to switch mount 21, and flexes in the lateral direction. However, it does not move up or down with respect to the handle. It is toggle plate 19 that moves up and down with respect to the handle. In FIG. 2, toggle switch 20 is flexed to its right-of-center position. Also partially visible in FIG. 2 is cylindrical barrel 30 nested in the bottom handle 18. As will be explained later, it is the rotation of this barrel about its longitudinal axis which causes the movements of the grippers 8, 9, and the arms 14, 15.

The toggle plate 19 and toggle 23 are preferably made of a rigid, medical grade plastic such as polyetherimide. The toggle switch 20 functions as a leaf spring biased in the central plane position which intersects the pivot 26 of the toggle 23 and is made of a spring material such as a rigid plastic or preferably, stainless steel.

Referring now to FIG. 3, the button 16 has been released so that the left and right gripper heads 10, 11 move proximally under spring force to hold the needle tightly against the left and right arm flanges 12, 13. The position of the left and right grippers as shown is hereinafter referred to as the "home" position. As can be seen, FIGS. 2 and 4 are identical because the trigger has not been actuated, only button 16 has been deactuated. Therefore, the toggle plate 19, toggle 23, and toggle switch 20 have not changed position.

Now that the surgeon has loaded the needle into the grippers 8 and 9, device 5 can be further explained by referring to FIG. 5. In this figure, the trigger has been pressed down by the surgeon, so that the trigger is now in what is hereinafter referred to as its "down" position. In this figure, the entire device has been rotated slightly about its longitudinal axis for clarity. By placing the trigger in its down position, the needle 1 has been released by left gripper 8 and arm 14 has rotated or spun about its longitudinal axis so that left arm distal end 83 has swung away from the right arm distal end 82. FIG. 18 shows a clear, perspective view of the distal portion of the present invention shown in FIG. 5. In this view it can be seen that the left gripper 8 has swung away from its home position and is open, thus allowing the surgeon to penetrate the tissue with the needle 1.

By referring to FIG. 6, one can see the movement of the toggle plate 19 and toggle 23. When the trigger is pressed down by the surgeon, the toggle plate 19 moves down within handle bottom 18, carrying toggle 23 with it. As a result, toggle plate rail 27 has moved down and away from toggle switch tip 22, allowing toggle switch 20 to spring laterally to its biased center position.

At this point in the sequence of operation, the needle is ready to be placed into the tissue using the same surgical technique as when using a conventional needle driver. While the trigger 17 is still being held down, the needle tip is placed against the tissue and the handle 6 is twisted clockwise about its longitudinal axis so that the needle tip penetrates the tissue and exits on the opposite side. This step is depicted in FIG. 24.

After the surgeon has penetrated the tissue he needs to pull the suture all the way through to make a stitch. This is done by returning the trigger to its up position and can best be described by referring to FIG. 7. As seen from that figure, the trigger 17 has been released to its up position so that the left gripper 8 has returned to its home position to grasp the needle 1, while right gripper 9 has maintained its grasp of needle 1, much in the way that it did in FIG. 3 However, by referring to FIG. 8, one can see that the toggle 23 and toggle switch 20 are in different positions than that shown in FIG. 4. As seen from this Figure, the toggle plate 19 has again moved upwardly with the trigger 17, carrying with it toggle 23. However, during this movement, toggle switch tip 22 now contacts left toggle surface 24 (see FIG. 4), causing toggle 23 to rotate counter clockwise as the trigger 17 is released to the up position.

Figure 9:
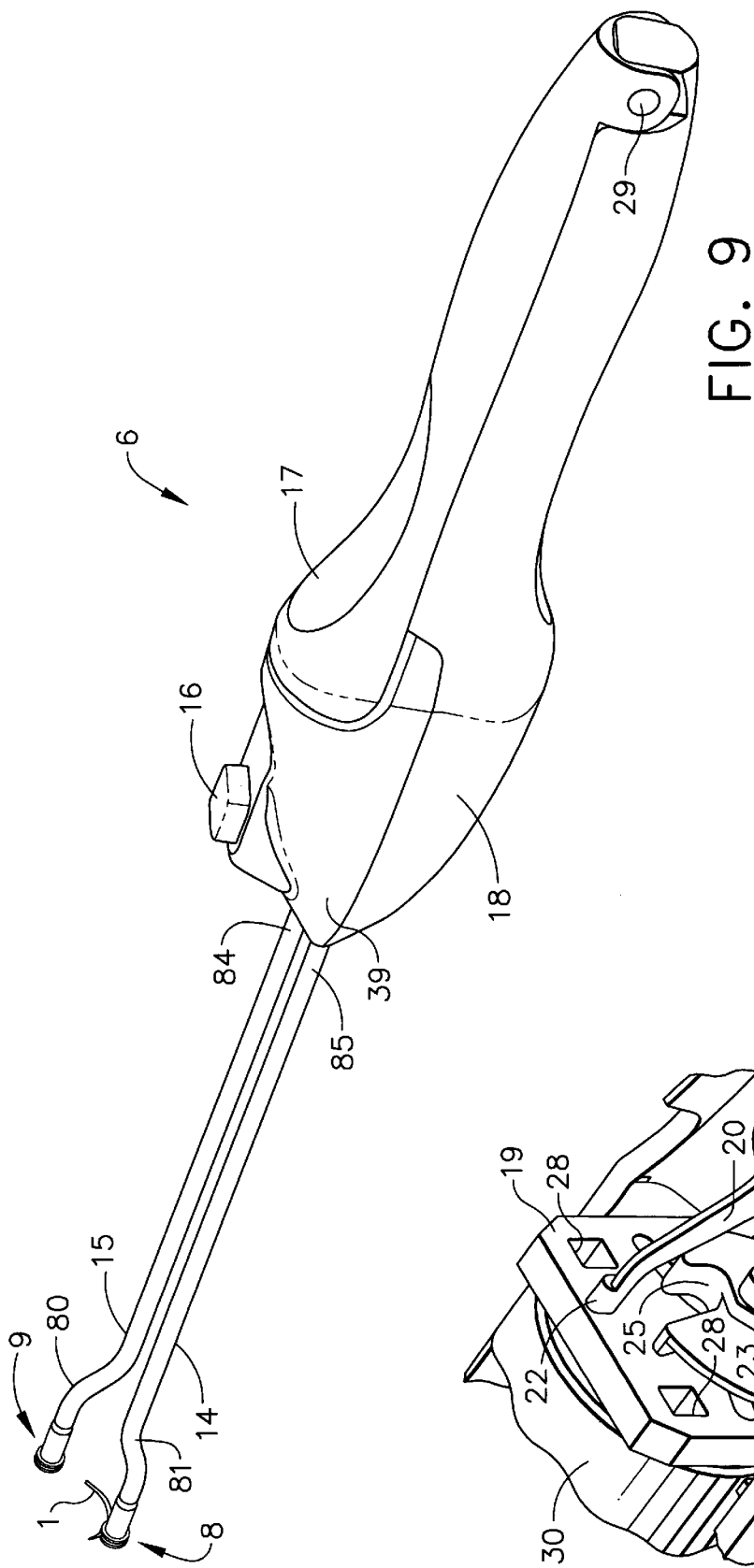
Figure 10:
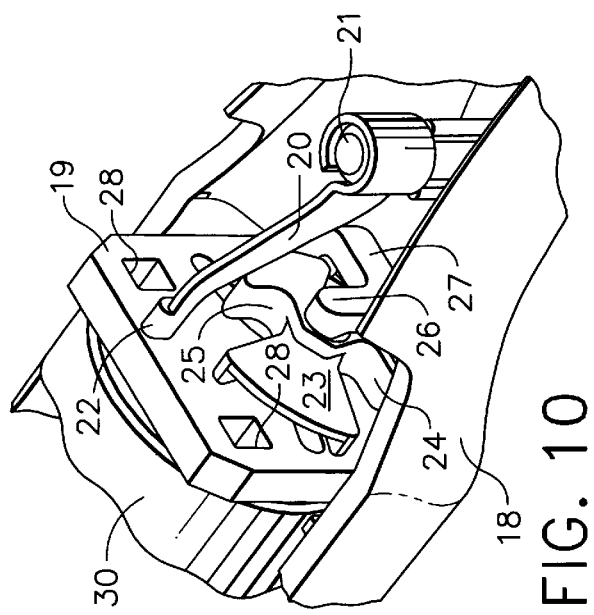

The next step of the operational sequence is the actuation of the trigger 17 to its down position again, as shown in FIG. 9. This causes the right gripper 9 to release the needle and causes arm 15 to rotate so that its distal end swings away from the left gripper 8. In this configuration, it is now possible for the surgeon to use the device like a conventional needle holder and to pull the needle 1 and its trailing suture (see the sequence of FIG. 24) out of the tissue, thus completing the stitch through tissue. Corresponding FIG. 10 shows the movement of the toggle plate 19 to its down position, allowing the toggle switch 20 to spring to its center biased position. The final step of the operational sequence is to release trigger 17 and is done after the distal end of the device is moved away from the tissue in order to allow the return of right gripper 9 to its home position as shown in FIG. 3. The toggle plate 19, the toggle 23, and the toggle switch 20 return also to the configuration shown in FIGS. 3 and 4, and the sequence may be repeated for another stitch into tissue.

Again, FIGS. 11A–11E show an end view of the left and right grippers 8, 9 and the needle 1 for each of the steps of the operational sequence shown in FIGS. 3, 5, 7, 9 and 3 again, respectively. For each step, the needle 1 is stationary with respect to the device handle 6; it is always one of the grippers 8, 9 which is moving to and from the needle 1.

In FIGS. 11A–11E it can be seen that each of the grippers, 8 and 9, move along an arcuate path either towards or away from the needle. For convention, the needle 1 shall be referred to as being above the grippers, 8 and 9. As depicted, the centers of these gripper arcuate motions approximately coincide with the center of curvature of the needle. The center of each gripper arcuate motion, however, does not necessarily need to coincide with the center of curvature of the needle. In fact, it is advantageous for the effective gripping of the needle that the center of arcuate motion of each gripper be offset from the center of curvature of the needle so that the gripper can approach the needle from underneath and be in position to grip the needle at a location on the needle slightly proximal to the needle end. This is advantageous to the surgeon for the following reason. As the needle is manipulated in tissue during the stitching procedure, the needle may deflect due to tissue loads or slip a small amount within the gripper. This deflection and/or slip may result in one of the ends of the needle to be in the path of one of the grippers as it moves downward towards the needle, as shown in FIGS. 11C and 11E. Then the gripper would hit against that needle end, preventing the gripper to complete its arcuate motion to the position where it can effectively grip the needle. In addition, the present invention is depicted herein as being used with a curved needle with the needle ends pointing up or away from the grippers, 8 and 9. It should be appreciated that for some needles of various curvatures, lengths, and shapes, the ends of the needle may be pointed down, or towards the grippers, 8 and 9. This feature allows the surgeon to load the needle into the grippers in an orientation most advantageous for the specific surgical procedure.

FIGS. 12A, 12B, 12C, and 12D are alternate views of FIGS. 2, 6, 8, 10, respectively. The toggle plate 19, toggle 23, switch 20, and barrel 30 are shown from the proximal end, and again depict the operational sequence. Note that for each step, barrel 30 remains centered on the X, Y reference frame axes 74, 75. It is the toggle plate 19 and toggle 23 which move vertically, causing toggle switch 20 to deflect laterally to the left or right of its centered position. Barrel 30 rotates either clockwise or counterclockwise due to its interaction with the up and down movement of the toggle plate 19. As will be explained below, rotation of the barrel causes the rotation of the arms 14 and 15 and the simultaneous actuation of grippers 8 and 9. The barrel as shown rotates upon the inside of the handle bottom 18. It should be appreciated that there are various other features that may be designed into the handle and/or onto the barrel in order to provide rotational support for the barrel, and that the embodiment shown is not intended to be limiting.

Figures 13A, 13C:
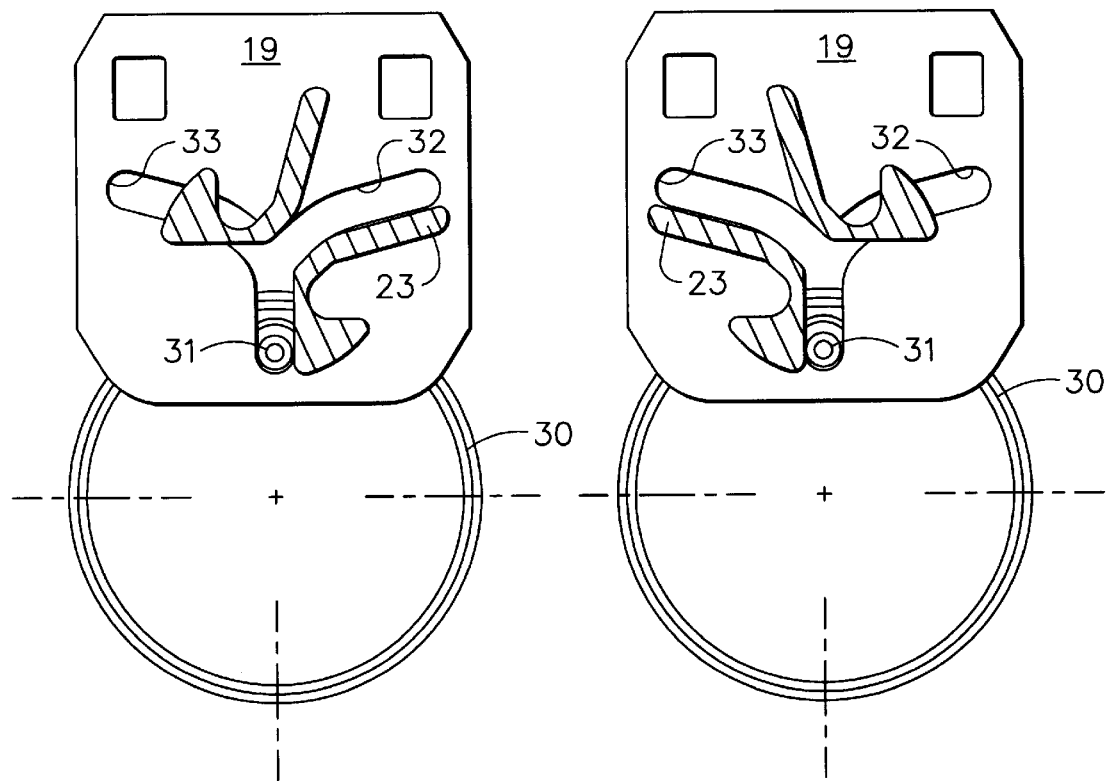
FIGS. 13A, 13B, 13C, and 13D are cut-away views of FIGS. 12A, 12B, 12C, and 12D, respectively.
Figures 13B, 13D:
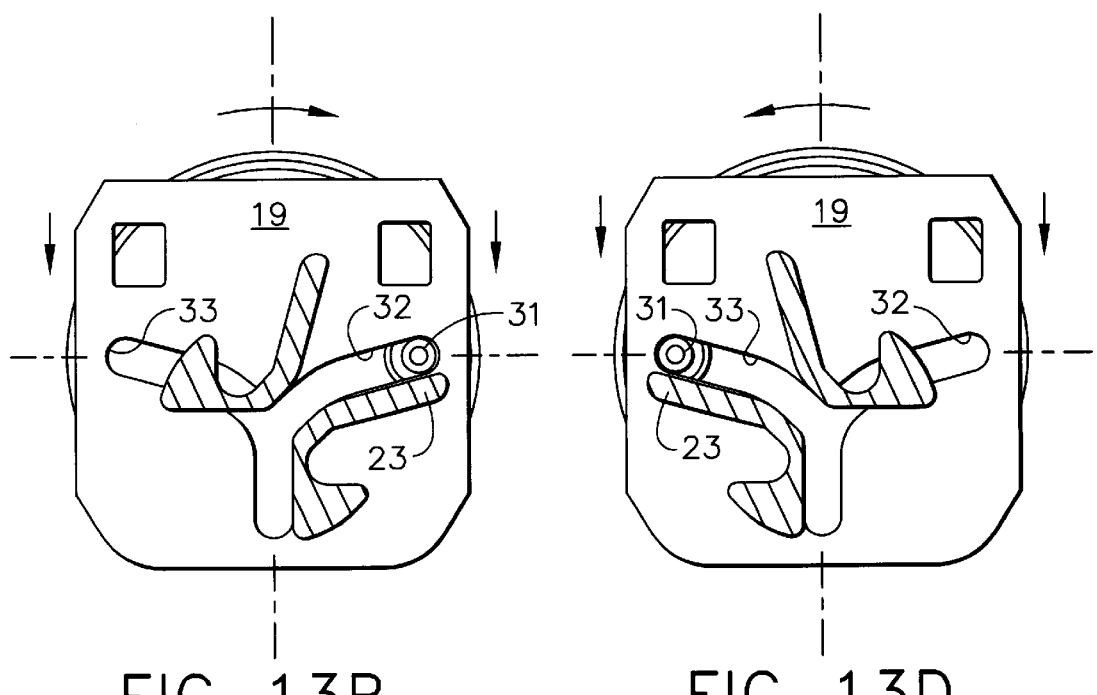

As seen from FIGS. 13A–13D, when the trigger is first actuated into the down position the barrel rotates clockwise about 90 degrees. When the trigger is released back into the up position, the barrel rotates counter clockwise about 90 degrees, back to its original position. Thereafter, when the trigger is again fired the barrel then rotates counter clockwise about 90 degrees and when released it rotates clockwise back to its original position. FIGS. 13A, 13B, 13C, and 13D correspond to FIGS. 12A, 12B, 12C, and 12D, respectively. The rotation of the barrel is accomplished by the fact that the barrel is connected to toggle plate by projection 31 and left and right toggle plate tracks 33, 32. When trigger 17 is actuated, the full clockwise orientation of the toggle 23 allows the barrel projection 31 to traverse the right toggle track 32 (FIG. 13B) while the full counterclockwise orientation of the toggle allows the barrel projection 31 to traverse the left toggle track 33 (FIG. 13D).

Figures 14A, 14B:
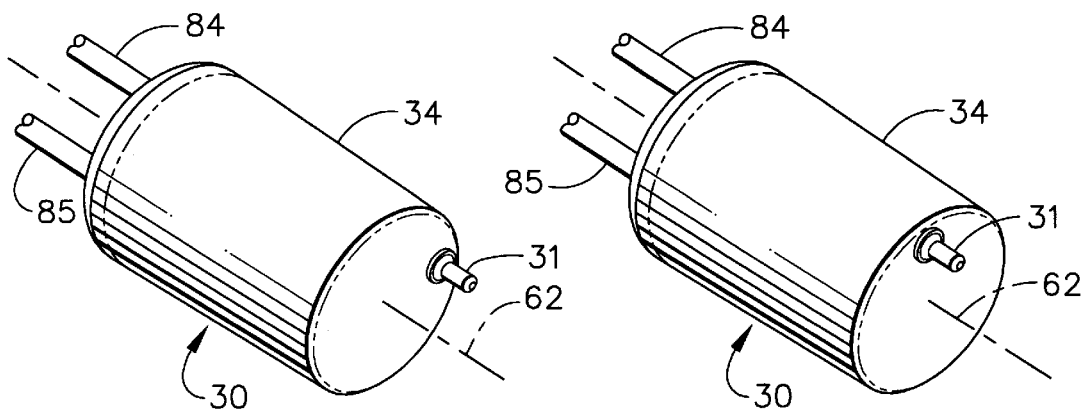
FIGS. 14A, 14B, and 14C are perspective views of the barrel for the clockwise, center, and counterclockwise positions, respectively.
Figure 14C:
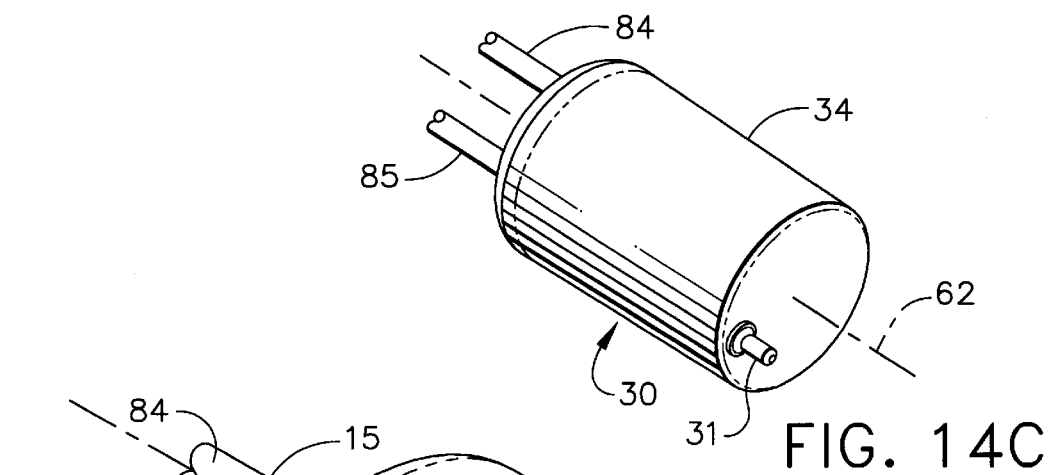

FIGS. 14A, 14B, and 14C show the three possible positions of the barrel projection 31 due to the interaction with the toggle plate 19 and the toggle 23 for when the trigger 17 is in the fully upward or fully downward position. FIG. 14A shows the full clockwise rotation about the longitudinal axis 62; FIG. 14B shows the center or "home" position of the barrel; FIG. 14C shows the full counterclockwise position. Partial views of the left arm proximal end 85 and the right arm proximal end 84 entering into the distal end of the barrel 30 are shown. As seen from these figures, the left and right arm proximal ends remain in a constant position with respect to each other. As mentioned before, movement of distal arm ends is caused by the rotation of the arms acting upon the offset bend sections 80, 81.

Figure 15:
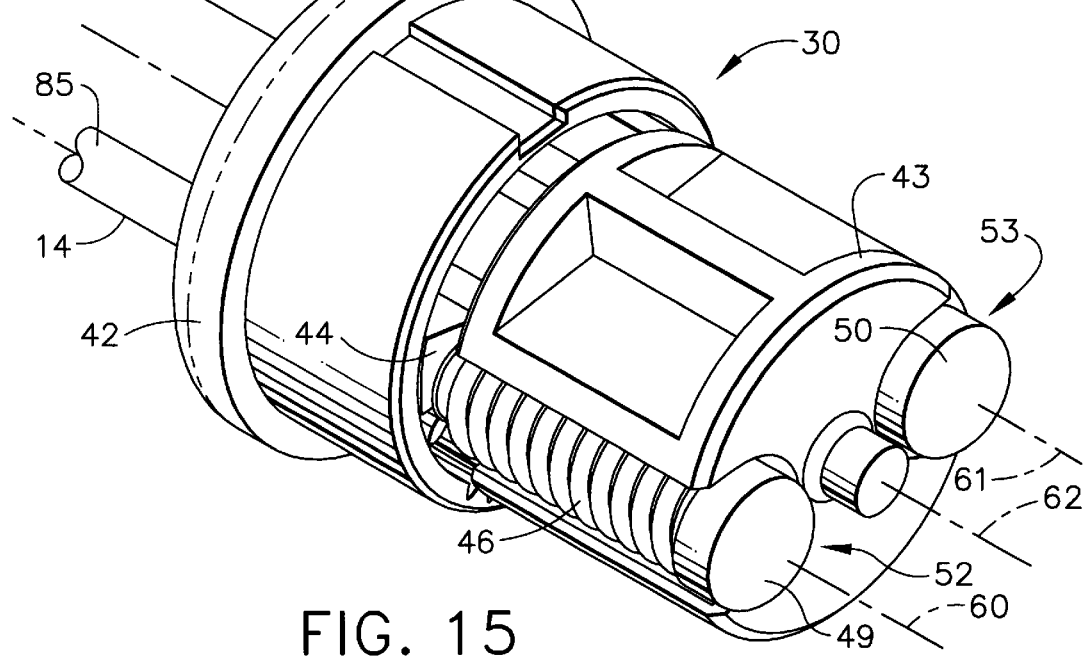
FIG. 15 is a enlarged, perspective view of the barrel depicted in FIG. 14B, but with the barrel cover removed for clarity.
Figure 16:
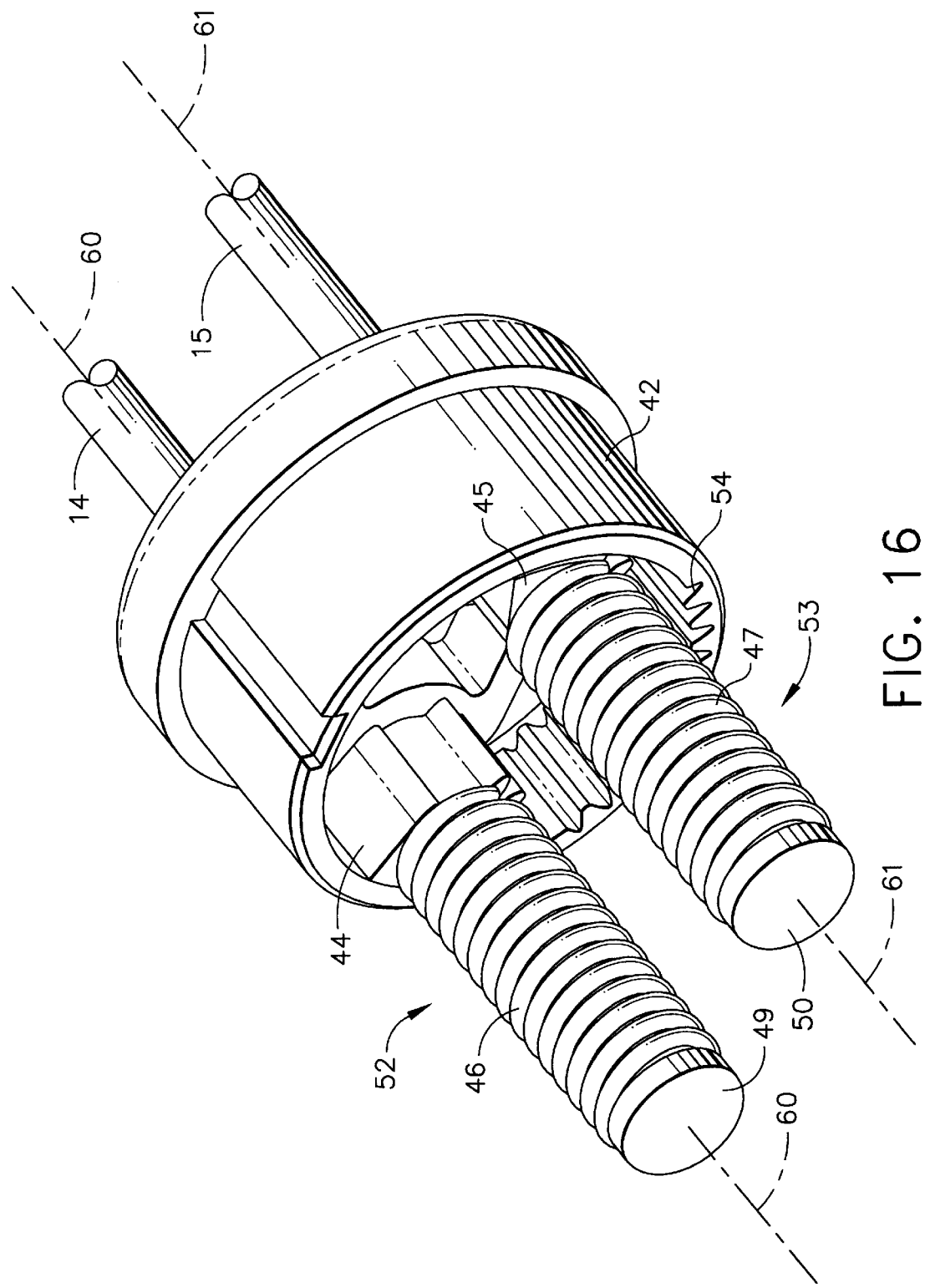
FIG. 16 is a perspective view of the barrel depicted in FIG. 14B, but with the barrel cover and yoke removed for clarity.

FIG. 15 corresponds with FIG. 14B and is a perspective view of the assembled components inside the barrel 30. Barrel cover 34 has been removed for clarity. Barrel 30 includes a yoke 43, preferably made from a rigid plastic. Cam lid 42 is made from a rigid plastic and fits tightly together with the barrel cover 34 to encapsulate the assembly. Yoke 43 houses a left pinion assembly 52 and a right pinion assembly 53. The following components of the left pinion assembly 52 are individually depicted in the exploded view of FIG. 23: a left pinion 44 which is attached to left arm proximal end 85; a left cam head 49 which may be metal or plastic and fits slideably into left pinion 44 and captures left pinion spring 46. Likewise, the right pinion assembly 53 includes a right cam head 50, right pinion spring 47 (not shown in FIG. 15), a right pinion 45 (also not shown in FIG. 15) and right arm proximal end 84. FIG. 16, wherein the yoke has been removed, has been presented to show the left and right pinion assemblies 52, 53 respectively as they interact with the inside of cam lid 42. Cam heads 49, 50 are attached to cables 40, 41, respectively, which are assembled slideably through longitudinal holes in pinions 44, 45.

Figure 17C:
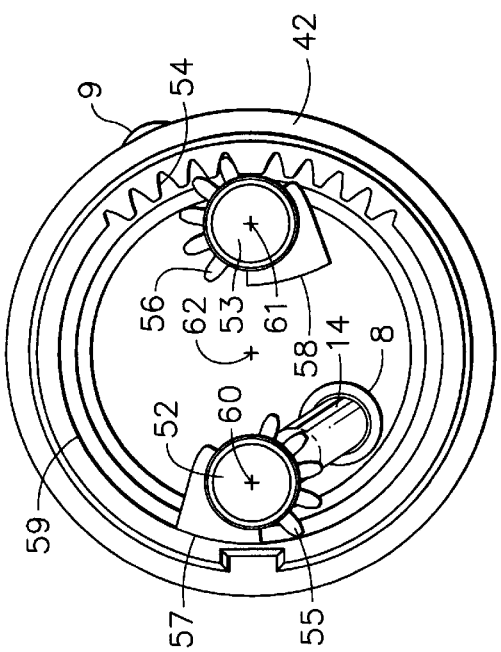
FIGS. 17A, 17B, and 17C are alternate views of the barrel depicted in FIGS. 14A, 14B, and 14C, respectively, with the barrel cover and yoke removed for clarity, and looking from the proximal end.
Figure 17B:
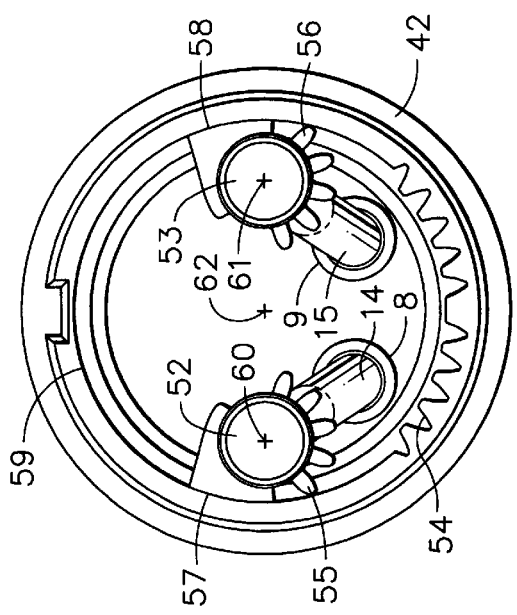
Figure 17A:
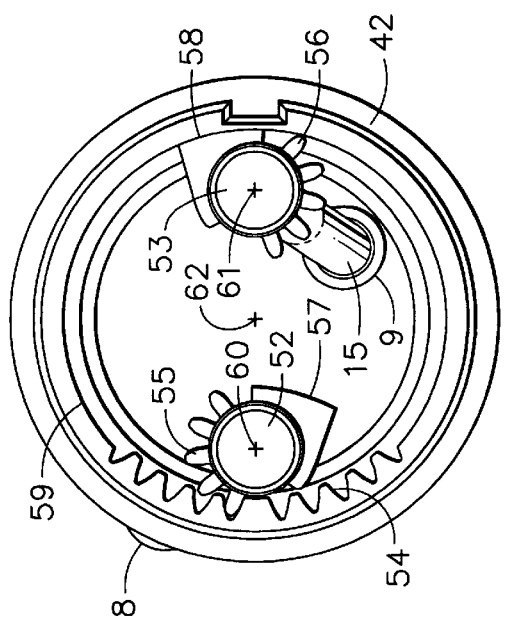

FIGS. 17A, 17B, 17C correspond with FIGS. 14A, 14B, and 14C, respectively, and show the proximal end of the components shown in FIG. 16. These figures are intended to show how the rotation of the barrel 30, and hence cam lid 42 due to their attachment to one another, causes the rotation of the left and right pinion assemblies 52, 53, which in turn causes the arms 14, 15 to rotate in order to swing grippers 8, 9 between their two end positions. In FIG. 17A, the cam lid 42 has been rotated to the full clockwise position due to the trigger actuation and the steps described in the preceding paragraphs. This cam lid position corresponds to FIGS. 5, 6, 12B, and 13B.

The cam lid gear teeth 54 mesh with the left pinion gear teeth 55 to cause the rotation of the pinion assembly 52 about its longitudinal axis 60 as the trigger is pressed into its down position. The rotation of pinion assembly 52 about its longitudinal axis 60 causes arm 14 to rotate which in turn causes left gripper 8 to swing to the position shown in FIGS. 5 and 11B. Simultaneously, right pinion sliding surface 58 of the right pinion assembly 53 slides along cam lid sliding surface 59, the right pinion assembly 53 therefore does not rotate about axis 61, and the right gripper 9 stays in its home position. The opposite interaction takes place when the cam lid 42 is caused to rotate counterclockwise as shown in FIG. 17C, causing right gripper 9 to swing away from its home position. FIG. 17B depicts the home position for both grippers 8, 9 and occurs when the cam lid gear teeth 54 are located in the central position and neither the left pinion gear teeth 55 or the right pinion gear teeth 56 are engaged.

Before the rotation of the left arm 14 takes place, causing the left gripper 8 to swing away from its home position, it is necessary for the left gripper 8 to release its hold of the needle 1, while the right gripper 9 maintains its grip. (See FIG. 19.) This is also true for the when the right arm 15 swings away from its home position, that is, the right gripper 9 must first release the needle 1. The timing for the actuation of grippers 8, 9 is designed accordingly, and is controlled by the cam mechanism within the barrel 30.

FIGS. 20A and 20B are longitudinal cross-sectional views of the barrel 30, cam lid 42, and yoke 43, containing the left and right pinion assemblies 52, 53, as configured in FIGS. 14A and 14C respectively, where the section for each was taken through a plane intersecting main axis 62 and barrel projection 31. Referring first to FIGS. 20A and 19, left arm proximal end 85 is attached to left pinion assembly 52 and right arm proximal end 84 is attached to right pinion assembly 53. Left and right pinion assemblies 52, 53 are shown in their relative positions within the barrel and are comprised of left and right cam heads 49, 50, and left and right pinion springs 46, 47, respectively. The left cam head 49 is attached to a left cable 40, which runs through the entire length of arm 14 where it is attached at its distal end to left gripper head 10, whereby all three components move together. Likewise, the right cam head 50 is attached to a right cable 41 which is attached to right gripper head 11 so that these three components move together. Compression springs 46 and 47 exert a longitudinal force such that cables 40 and 41 are usually, unless as otherwise noted below, under tension.

Cables 40, 41 are flexible in order to move easily in the longitudinal direction through the offset of the distal portion of the left and right arms 14, 15 respectively, and may be made of a semi-rigid plastic or of metal wire strands. The cables are constrained in the channels within the arms so that they also can transmit a compressive force sufficient for moving the gripper heads distally.

In FIGS. 20A, 20B it can be seen that the barrel 30 has a peripheral cam surface 64 at its proximal end. Cam surface 64 is always in contact with the left and right cam heads 49 and 50, and the right and left pinion cam surfaces 67, 68 are always in contact with the cam lid peripheral cam surface 66, due to the longitudinally outward force of the left and right pinion springs 46 and 47.

In FIG. 20A the barrel is rotated in the full clockwise position, as also shown in FIGS. 6, 12B, 13B, 14A, and 17A. The right pinion spring 47 is assembled into the barrel partially compressed and is shown in FIG. 20A for when it has its maximum allowable length. The longitudinal force of the spring has caused the right cam head 50 to move proximally, thereby moving cable 41 and right gripper head 9 proximally. Simultaneously, right pinion 53 has moved distally, causing right arm 15 and right arm flange 13 to move distally. These two, opposing movements provide a bi-directional grip on the needle 1. Again in FIG. 20A, the left pinion spring 46 is at its minimum allowable length because the left arm 14 was moved in the proximal direction and the left cam head 49 was moved in the distal direction. This results in the bi-directional separation of the left gripper head 10 and the left arm flange 12 as can be seen in FIG. 19. This separation feature is advantageous because the needle is centered on the gap between the gripper head 10 and arm flange 12, and therefore allowable variation of needle alignment with the gap is greater than if only the gripper head 10 or the arm flange 12 were to move alone. This feature facilitates "catching" of the needle. FIG. 20B shows the opposite configuration to that of FIG. 20A and corresponds to FIG. 14C for when the barrel 30 is rotated to the full counterclockwise position. The needle is gripped in the left gripper 8 and released by right gripper 9, just prior to right arm 15 swinging away from the home position.

Figure 21:
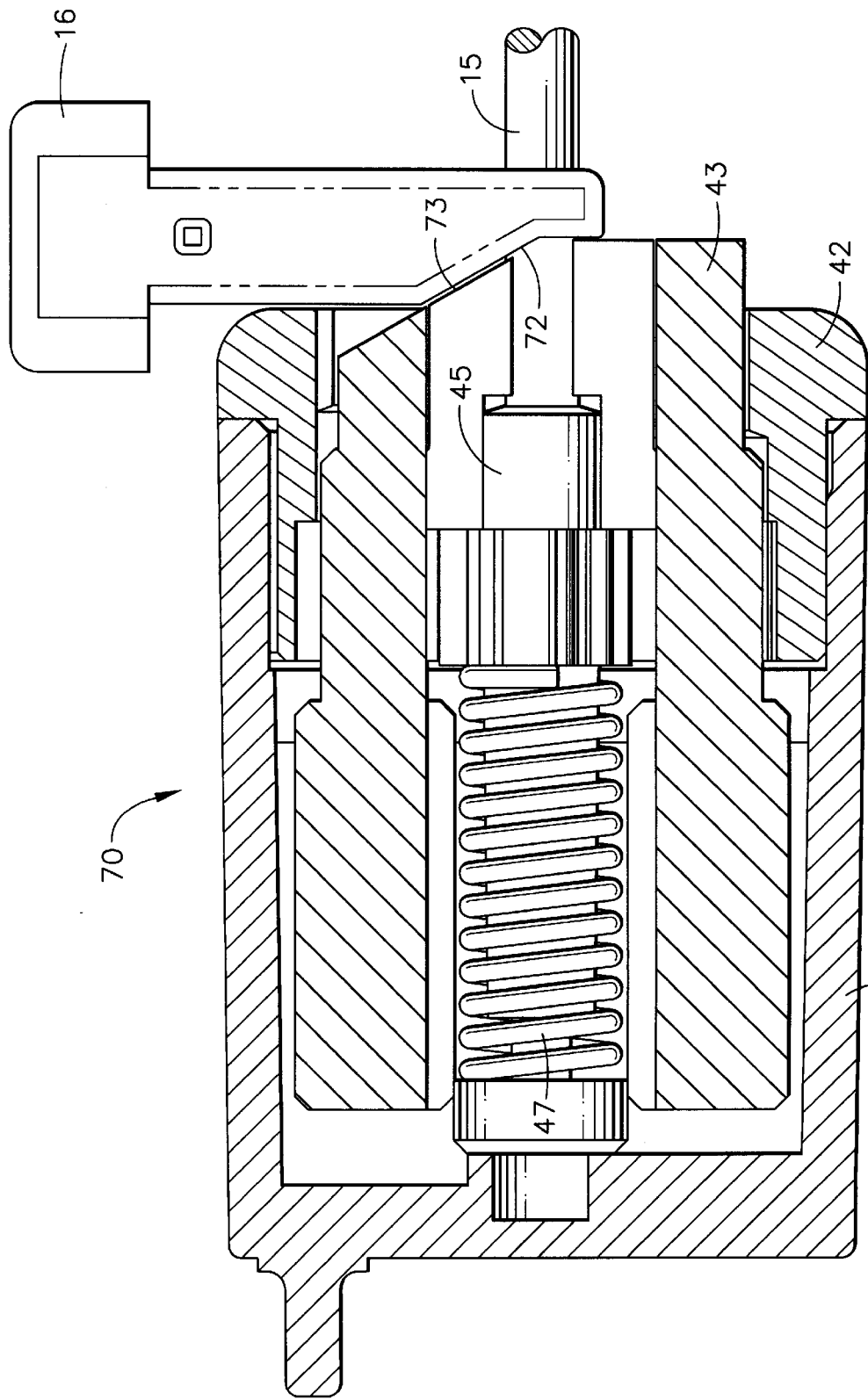
FIG. 21 is a side, cross-sectional view of the barrel together with the loading button in the up position as depicted in FIG. 2 for the present invention.
Figure 22:
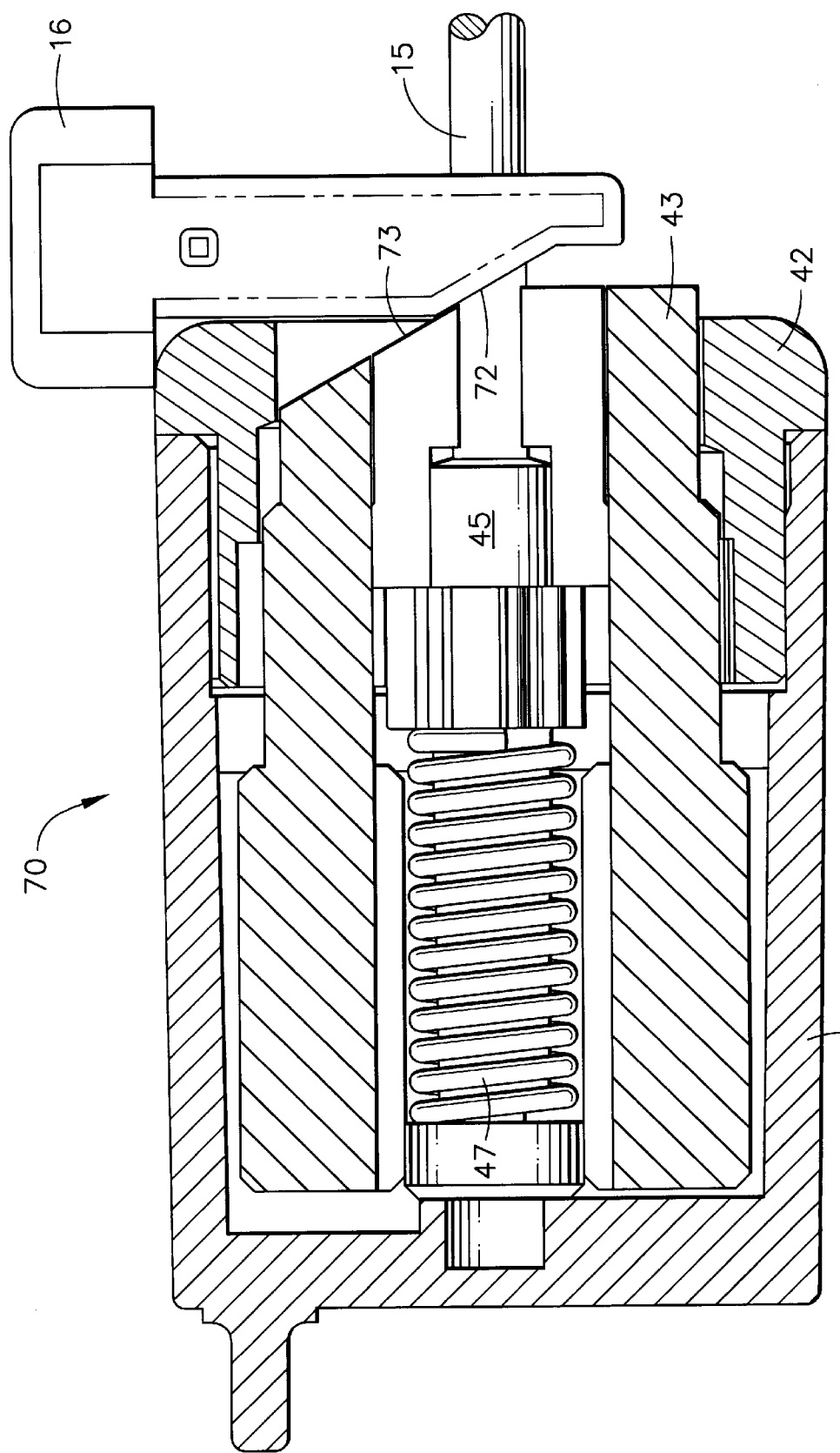
FIG. 22 is a side, cross-sectional view of the barrel together with the loading button in the down or actuated position and corresponds to the present invention as depicted in FIG. 1.

Now turning to FIGS. 21 and 22, the operation of the button 16 for the loading and release of needle 1 from the distal end of the present invention is next described. In FIG. 21, which corresponds to FIG. 3, the needle 1 is gripped by both the left gripper 8 and the right gripper 9, both in the home position, the button 16 is in the full upward or non-actuated position . It is held there by the spring forces exerted by the left and right pinion springs 46, 47 pushing simultaneously against left and right cam heads 49, 50, and against the left and right pinions 44, 45, which in turn impart a longitudinally directed force on the yoke 43 in the distal direction. A yoke ramp surface 73 transmits this force to the button ramp surface 72, forcing the button 16 vertically upwards. In FIG. 22 which corresponds to FIG. 1 when the needle I may be loaded into or released from the grippers 8, 9, the button 16 is pushed downwards by the surgeon, imparting a longitudinal force in the proximal direction onto the yoke 43, which in turn bears against left and right pinions 44, 45, causing them to move in the proximal direction against the spring forces exerted by left and right pinion springs 44, 45, and finally resulting in the movement in the proximal direction of left and right arms 14, 15 which are attached to left and right pinions 44, 45. Thus, the respective gaps between the gripper heads 10, 11 and the arm flanges 12, 13 increase equally to a width greater than the diameter of the needle being used. The interfacing button ramp surface 72 and yoke ramp surface 73 also serve to key the yoke 43 so that it does not rotate when the trigger 17 is actuated and the barrel 30 and cam lid 42 rotate within the stationary handle bottom 18 and handle top 39.

Although particular embodiments of the present invention have been shown and described, modification may be made to the device without departing from the spirit and scope of the present invention. The terms used in describing the invention are used in their descriptive sense and not as terms of limitations.

What is claimed is:

1. A method for suturing tissue, said method comprising:

a) providing a device comprising a handle for holding said device, said handle having distal and proximal ends, right and left arms extending distally from said handle, said arms having proximal ends attached to said handle and distal ends having grippers attached thereto for gripping and releasing a needle, and at least one mechanism for moving said distal ends of said arms closely adjacent to one another, by rotating at least one of said arms, and for passing said needle from one gripper to the other and thereafter for moving said distal ends of said arms further apart from one another, by rotating at least one of said arms, said right gripper holding a needle having a suture attached thereto;

b) manually placing a distal end of said needle through said tissue;

c) rotating at least one of said arms by actuating said at least one mechanism so as to move said arms closely adjacent one another so that said left gripper holds said needle, said right gripper releases said needle, and moving said distal ends of said arms further apart from one another; and d) removing said needle from said tissue.

2. The method according to claim 1 further including the step of moving said distal ends of said arms apart from one another prior to step (b).

3. The method according to claim 1 wherein steps (b through (d) are repeated a plurality of times.

4. The method according to claim 1 wherein step (d) is done manually.

* * * * *